United States Patent [19]

Hussain

[11] Patent Number: 4,464,378

[45] Date of Patent: Aug. 7, 1984

[54] METHOD OF ADMINISTERING NARCOTIC ANTAGONISTS AND ANALGESICS AND NOVEL DOSAGE FORMS CONTAINING SAME

[75] Inventor: Anwar A. Hussain, Lexington, Ky.

[73] Assignee: University of Kentucky Research Foundation, Lexington, Ky.

[21] Appl. No.: 258,308

[22] Filed: Apr. 28, 1981

[51] Int. Cl.$^3$ .......................................... A61K 31/485
[52] U.S. Cl. ............................ 424/260; 260/239 BB; 546/44; 546/45; 546/46; 546/61
[58] Field of Search .................. 424/260; 260/239 BB

[56] References Cited

U.S. PATENT DOCUMENTS 4,275,059  6/1981  Flora et al. ......................... 424/230

Primary Examiner—Stanley J. Friedman
Attorney, Agent, or Firm—Burns, Doane, Swecker & Mathis

[57] ABSTRACT

The invention provides a novel method of administering narcotic antagonists, narcotic analgesics and related compounds, and novel dosage forms containing those compounds which are adapted for nasal administration. The nasal dosage forms disclosed include solutions, suspensions, gels and ointments. Especially preferred compounds which can be advantageously administered in accordance with the invention include naloxone, naltrexone, nalbuphine, levorphanol, buprenorphine, butorphanol, $\Delta^9$-tetrahydrocannabinol (THC), cannabidiol (CBD) and levonantradol.

51 Claims, 1 Drawing Figure

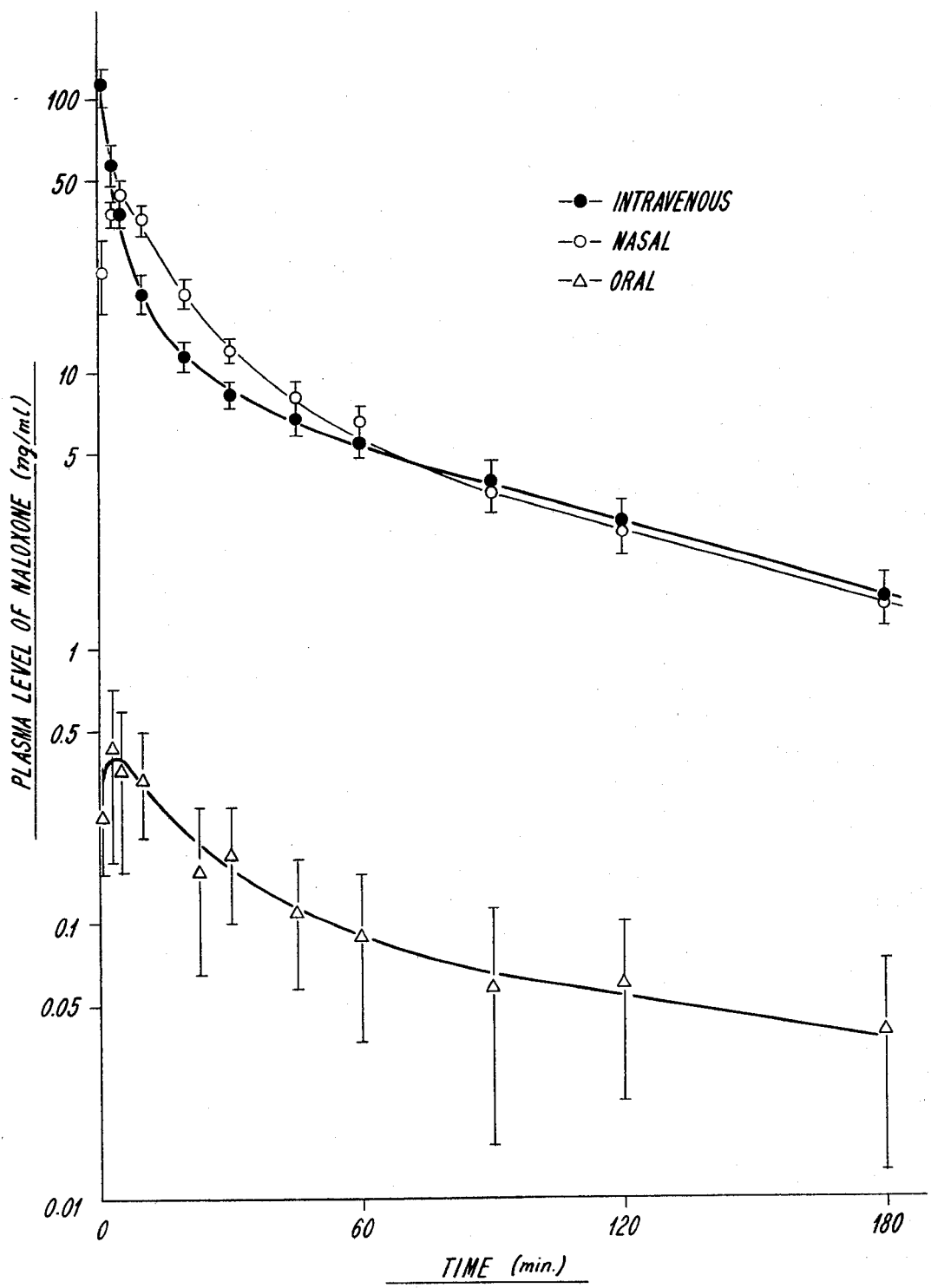

METHOD OF ADMINISTERING NARCOTIC ANTAGONISTS AND ANALGESICS AND NOVEL DOSAGE FORMS CONTAINING SAME

BACKGROUND OF THE INVENTION

1. Field of the Invention

The present invention relates to a novel method of administering narcotic antagonists, narcotic analgesics and related compounds, and to novel dosage forms containing such compounds adapted for nasal administration.

2. Background Art

Morphine, which has the structural formula

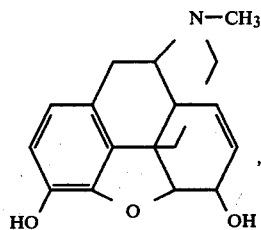

is a potent narcotic analgesic which is principally used to relieve pain; it is also used in the dyspnea of heart failure, in pulmonary edema and cough, as a sedative and in the control of diarrhea (chiefly in the form of paragoric). Morphine causes both depression and stimulation in the central nervous system and the gut, its most significant actions being analgesia, hypnosis, respiratory depression, smooth muscle spasm, nausea, vomiting and circulatory and other effects (especially miosis). The drug is well-absorbed by injection, but absorption via the oral route is inefficient and variable, probably because of metabolism in the liver, chiefly by conjugation with glucuronic acid. Abuse leads to habituation or addiction.

The morphine molecule has been subjected to a variety of structural modifications in efforts to enhance selected properties and/or to deemphasize others, as well as to produce drugs which actually antagonize the effects of morphine and other opioid analgesics. Such efforts have led to the development of a variety of classes of chemical compounds, such as the class of morphine analogues whose structures are very closely allied to that of morphine, retaining both the phenolic OH and the N-methyl substituent of morphine, such as apomorphine, levorphanol and oxymorphone, and which as a group have strong analgesic, respiratory depressant and smooth muscle stimulant activity but which also are highly addicting. Retention of the phenolic hydroxyl while replacing the methyl on the nitrogen atom with a larger alkyl or similar side-chain has afforded both morphine analogues which are relatively pure opioid antagonists (e.g. naloxone and naltrexone) and are used in the treatment of narcotic-induced respiratory depression (overdose), in the diagnosis of narcotic addiction and in the prophylaxis of narcotic abuse; and morphine analogues which are agonist-antagonists (e.g. buprenorphine, pentazocine, nalorphine and cyclazocine), which display varying degrees of morphine-like activity as well as of morphine-antagonist behavior, and which can therefore be used as analgesics as well as for the purposes for which the relatively pure antagonists are used. Buprenorphine appears to be a particularly valuable analogue because of its low physical dependence potential, as well as its potent narcotic antagonist and analgesic activity. See Cowan et al, *Br. J. Pharmac.* (1977), 60, 537–545; Jasinski et al, *Arch. Gen. Psychiatry,* Vol. 35, April 1978, 501–516; Mello et al, *Science,* Vol. 207, Feb. 8, 1980, 657–659.

Virtually all of the members of the groups of morphine analogues discussed supra are well-absorbed by injection, but are rarely used orally because of inefficient and variable absorption by that route. The low effectiveness of naloxone when taken orally has been attributed to the rapid and almost total formation of a less active metabolite in the first hepatic transit. See Fishman et al, *J. Pharmacol. Exp. Ther.* 187, 575–580 (1973). Also Berkowitz et al, *J. Pharmacol. Exp. Ther.* 195, 499–504, and the references cited therein.

Yet other structural modifications of the morphine molecule have resulted in codeine and its analogues; methadone and related compounds; and meperidine and related compounds such as profadol. Also see, generally, *Pharmacological Basis of Therapeutics,* ed. Goodman and Gilman, sixth edition, Chapter 22, "Opioid Analgesics and Antagonists", by Jaffe and Martin, pp. 494–534 (MACMILLAN PUBLISHING CO., INC., New York, 1980); *Cutting's Handbook of Pharmacology,* sixth edition, ed. T. Z. Czáky, M.D., Appleton-Century-Crofts/New York, Chapter 50, pp. 551–571.

Recent studies of THC, or $\Delta^9$-tetrahydrocannabinol, which is the active ingredient in marijuana, or its derivatives (e.g. CBD or cannabidiol, and levonantradol) suggest that these compounds are potentially useful in a wide variety of therapeutic areas, such as in the prevention of narcotic withdrawal symptoms and as antiemetics, particularly in the treatment of cancer patients undergoing chemotherapy. Unfortunately, oral administration has been found to be much less effective than intramuscular injection. See, *Medical News,* Monday, Jan. 19, 1981, page 3, for a more detailed discussion of the various therapeutic uses of THC and its derivatives.

SUMMARY OF THE INVENTION

In view of the foregoing, it is apparent that a serious need exists for the improved delivery of narcotic antagonists, narcotic analgesics and related compounds which are not well-absorbed orally. Thus, it is an object of the present invention to provide novel dosage forms and a novel method of administering morphine or an analogue thereof bearing at least one phenolic hydroxyl substituent and having narcotic analgesic, antagonist or agonist-antagonist activity, or $\Delta^9$-tetrahydrocannabinol or a pharmacologically active analogue thereof bearing at least one phenolic hydroxyl substituent, which will provide greatly enhanced bioavailability as compared to oral administration, while at the same time providing relative ease of administration when compared to intramuscular, subcutaneous or intravenous injection. This object is achieved by nasal administration of morphine, $\Delta^9$-tetrahydrocannabinol, or one of their aforesaid phenolic, pharmacologically active analogues, advantageously formulated into a solution, suspension, ointment or gel adapted for nasal administration.

BRIEF DESCRIPTION OF THE DRAWING

The FIGURE of the drawing is a semi-logarithmic plot of mean plasma levels of naloxone after intravenous, nasal and oral administration of a dose of 30 μg of naloxone per rat.

DETAILED DESCRIPTION OF THE INVENTION

The narcotic analgesics, narcotic antagonists and narcotic agonist-antagonists intended for use in the compositions and method of the present invention include morphine and pharmacologically active analogues thereof having at least one aromatic ring, said ring bearing at least one free OH group. Particularly significant morphine analogues contemplated by the present invention include morphine-like analgesics such as apomorphine, hydromorphone, levorphanol, metopon and oxymorphone; and narcotic antagonists and agonist-antagonists such as buprenorphine, diprenorphine, butorphanol, cyclazocine, pentazocine, phenazocine, levallorphan, nalorphine, naloxone, alazocine, nalbuphine, oxilorphan, nalmexone and naltrexone. Other analogues contemplated by the invention included ketobemidone, apocodeine, profadol, cyclorphan, cyprenorphine, desomorphine, dihydromorphine, 3-hydroxy-N-methylmorphinan, levophenacylmorphan, metazocine, norlevorphanol, oxymorphone, phenomorphan, pholcodine and hydroxypethidine. Especially preferred morphine analogues are those having antagonist or agonist-antagonist properties, especially naloxone, nalbuphine, naltrexone, buprenorphine and butorphanol. Any pharmaceutically acceptable form of morphine or of its phenolic analogues can be used, i.e. the free base or a pharmaceutically acceptable acid addition salt thereof (e.g. naloxone hydrochloride, nalbuphine hydrochloride, nalorphine hydrochloride, nalorphine hydrobromide, levallorphan tartrate, morphine sulfate, levorphanol tartrate, buprenorphine hydrochloride, butorphanol tartrate, pentazocine lactate, pentazocine hydrochloride, phenazocine hydrobromide, morphine hydrochloride, profadol hydrochloride, etc.); generally, the selected compound is employed in the instant compositions and method in the pharmaceutically acceptable form which has previously been found most advantageous for use by injection or orally. The structural formulae for representative free bases encompassed by the present invention are set forth below:

apomorphine

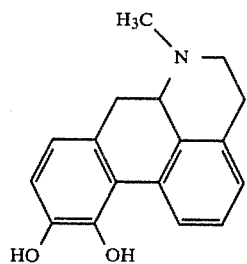

levorphanol

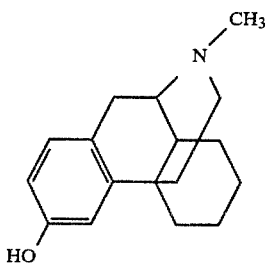

oxymorphone

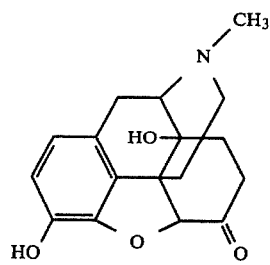

buprenorphine

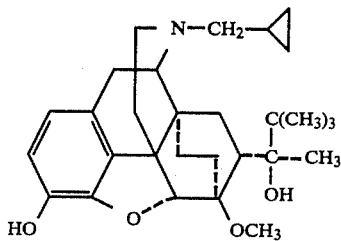

butorphanol

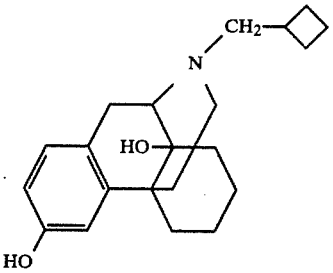

cyclazocine

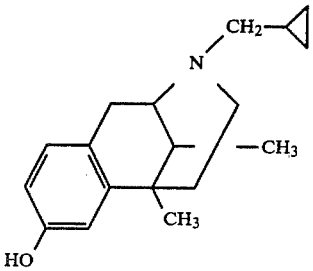

pentazocine

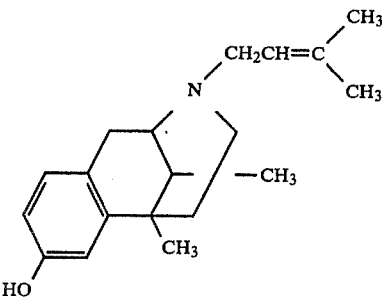

phenazocine
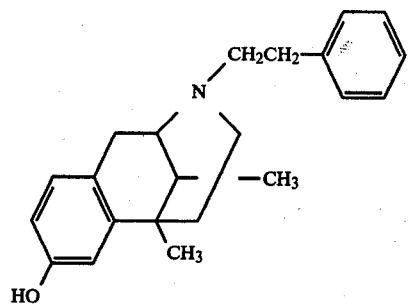

nalorphine
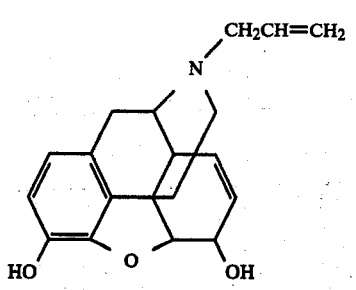

levallorphan
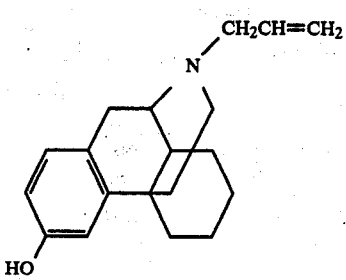

naloxone
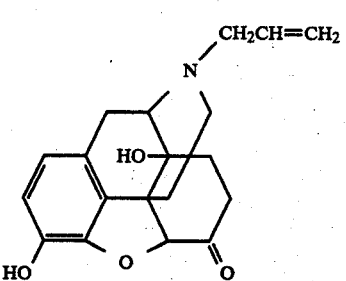

nalbuphine
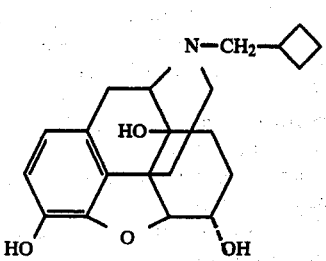

naltrexone
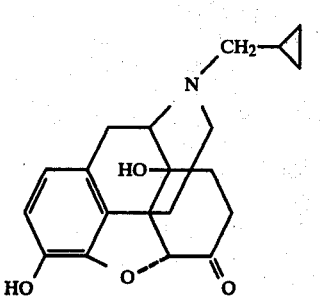

profadol
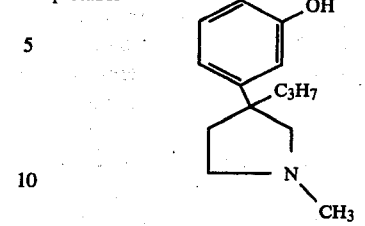

These morphine analogues and their salts can be prepared by well-known methods. Morphine itself can of course be isolated from natural sources and then converted, if desired, into a pharmaceutically acceptable acid addition salt.

The cannabinoids intended for use in the method and compositions of the present invention include $\Delta^9$-tetrahydrocannabinol (THC) and pharmacologically active derivatives thereof having at least one free OH group on an aromatic ring thereof. $\Delta^9$-Tetrahydrocannabinol has the structural formula

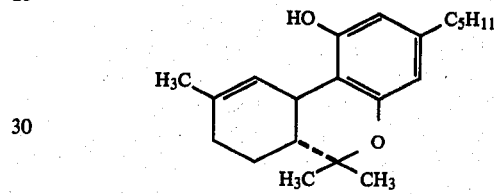

Preferred derivatives thereof for use in the present invention include cannabidiol (CBD) and levonantradol. These compounds can be prepared by known methods or, in the case of THC and CBD, isolated from natural sources.

In accord with the present invention, morphine, THC and their pharmacologically active phenolic analogues can be administered nasally with results considerably superior to those obtained with oral administration in terms of enhanced drug bioavailability and minimization of blood level variations, thus enabling use of these drugs at the dosage levels previously possible only by injection without the disadvantages inherent in subcutaneous, intrasmuscular or intravenous administration. It would appear that these drugs are rapidly absorbed from the nasal mucosa into systemic blood without extensive metabolism in the gastrointestinal tract and/or extensive first-pass metabolism.

The following study was undertaken to examine the bioavailability of a representative drug employed in the method and compositions of the invention, namely naloxone, administered nasally, in comparison with the bioavailability of that drug when administered orally and intraveneously.

Sprague-Dawley male rats, each weighing about 270 grams, were used in the study. Three groups of three rats each were employed, one group for each route of administration. The rats were anesthetized with pentobarbital (50 mg/kg) prior to administration of the drug. Naloxone was administered at a dose of 30 μg/rat (∼40 μCi/rat) as $^3$H-naloxone in 0.1 ml of isotonic saline. For intravenous administration, the drug was injected through the femoral vein. For oral (intraduodenal) administration, the abdomen of each rat was opened through a midline incision and the drug was injected directly through the duodenum. For nasal administration, an incision was made in the neck of each rat and the trachea was cannulated with a polyethylene tube. Another tube was inserted from the esophagus to the posterior part of the nasal cavity, and the nasoplantine was closed with an adhesive agent to prevent drainage of the drug from the nasal cavity to the mouth. The drug was then administered to the nasal cavity through the tube by means of a syringe. Blood was sampled periodically from the femoral aorta. Unchanged radiolabelled naloxone was analyzed according to the procedure described by Fishman et al, *J. Pharmacol. Exp. Ther.* 187, 575–580 (1973). The method involved centrifugation of the blood and spiking the plasma samples with cold naloxone. The drug was then extracted from the plasma with ethyl acetate. The ethyl acetate extract was then spotted onto thin layer chromatographic plates and the plates were developed in a 100:60:2 chloroform-methanol-acetic acid system (parts by volume). The zone corresponding to free naloxone visualized by ultraviolet absorption was removed and the radioactivity counted.

TABLE I below shows the individual plasma level data of naloxone from intravenous (PART A), nasal (PART B) and oral (PART C) routes, while the figure of drawing shows the mean plasma levels of naloxone for the different routes of administration. TABLE II below shows the area under the curve values (AUC 0) for the individual rats for each of the three routes of administration, the bioavailability calculated for the nasal and oral routes, and the half-lives of elimination of the drug after intravenous and nasal administration.

TABLE I

| Time (Min.) | Plasma Level (ng/ml) | | | | |
|---|---|---|---|---|---|
| | I | II | III | Mean | SE |
| PLASMA LEVELS OF NALOXONE AFTER INTRAVENOUS ADMINISTRATION OF 30 μg/RAT (40 μCi/RAT) OF $^3$H—NALOXONE IN INDIVIDUAL RATS | | | | | |
| 1 | 101.65 | 91.45 | 138.57 | 110.56 | 14.31 |
| 3 | 52.28 | 44.00 | 77.77 | 58.02 | 10.16 |
| 5 | 31.38 | 33.03 | 47.93 | 37.45 | 5.26 |
| 10 | 15.60 | 16.92 | 26.34 | 19.62 | 3.38 |
| 20 | 10.27 | 11.44 | 13.01 | 11.57 | 0.79 |
| 30 | 7.28 | 9.16 | 8.59 | 8.34 | 0.56 |
| 45 | 5.47 | 7.98 | 6.77 | 6.74 | 0.72 |
| 60 | 4.87 | 5.82 | 5.54 | 5.41 | 0.28 |
| 90 | 3.01 | 4.63 | 4.23 | 3.96 | 0.49 |
| 120 | 2.15 | 3.87 | 2.57 | 2.86 | 0.52 |
| 180 | 1.25 | 1.77 | 1.40 | 1.47 | 0.15 |
| PLASMA LEVELS OF NALOXONE AFTER NASAL ADMINISTRATION OF 30 μg/RAT (40 μCi/RAT) OF $^3$H—NALOXONE IN INDIVIDUAL RATS | | | | | |
| 1 | 36.20 | 12.71 | 20.97 | 23.29 | 6.88 |
| 3 | 41.21 | 30.85 | 42.80 | 38.29 | 3.75 |
| 5 | 54.45 | 33.41 | 44.15 | 44.00 | 6.07 |
| 10 | 45.30 | 31.53 | 31.02 | 35.95 | 4.68 |
| 20 | 22.73 | 17.68 | 17.99 | 19.47 | 1.63 |
| 30 | 13.46 | 11.83 | 10.79 | 12.03 | 0.78 |
| 45 | 9.36 | 7.95 | 6.56 | 7.96 | 0.81 |
| 60 | 8.26 | 5.98 | 4.98 | 6.41 | 0.97 |
| 90 | 4.79 | 3.16 | 2.80 | 3.58 | 0.61 |
| 120 | 3.65 | 2.29 | 1.84 | 2.59 | 0.54 |
| 180 | 1.95 | 1.22 | 1.10 | 1.42 | 0.27 |

TABLE I (PART C)
PLASMA LEVELS OF NALOXONE AFTER ORAL ADMINISTRATION OF 30 μg/RAT (40 μCi/RAT) OF $^3$H—NALOXONE IN INDIVIDUAL RATS

| Time (Min.) | Plasma Level (ng/ml) | | | | |
|---|---|---|---|---|---|
| | I | II | III | Mean | SE |
| 1 | 0.22 | 0.10 | 1.43 | 0.25 | 0.10 |
| 3 | 0.44 | 0.15 | 0.74 | 0.44 | 0.30 |
| 5 | 0.18 | 0.30 | 0.64 | 0.37 | 0.24 |
| 10 | 0.22 | 0.15 | 0.64 | 0.34 | 0.15 |
| 20 | 0.19 | 0.03 | 0.25 | 0.16 | 0.11 |
| 30 | 0.28 | 0.10 | 0.17 | 0.18 | 0.09 |
| 45 | 0.13 | 0.05 | 0.16 | 0.11 | 0.06 |
| 60 | 0.10 | 0.02 | 0.14 | 0.09 | 0.06 |
| 90 | 0.04 | 0.03 | 0.12 | 0.06 | 0.05 |
| 120 | 0.03 | 0.06 | 0.10 | 0.06 | 0.04 |
| 180 | 0.03 | 0.02 | 0.07 | 0.04 | 0.03 |

TABLE II

AREA UNDER THE BLOOD LEVEL CURVE VALUES (AUC 0) FOR INDIVIDUAL RATS FROM THE THREE ROUTES OF ADMINISTRATION OF NALOXONE AND HALF-LIVES OF ELIMINATION OF NALOXONE FOLLOWING INTRAVENOUS AND NASAL ADMINISTRATION

| | I | II | III | Mean | SE | $t_{\frac{1}{2}}$ |
|---|---|---|---|---|---|---|
| IV | 1269.7 | 1540.5 | 1685.8 | 1498.7 | 121.9 | 59.2 min. |
| Nasal | 1904.2 | 1336.2 | 1312.0 | 1517.5 | 193.5 | 52.1 min. |
| Oral | 19.1 | 11.3 | 35.5 | 22.0 | 7.1 | — |

BIOAVAILABILITY CALCULATIONS:

$$\frac{AUC\ nasal}{AUC\ iv} \times 100 = 1.013 \times 100 = 101.3\%$$

$$\frac{AUC\ oral}{AUC\ iv} \times 100 = 0.015 \times 100 = 1.5\%$$

It can be seen from TABLE II that the areas under the curve following intravenous and nasal administration were not significantly different, i.e. absorption of naloxone via the nasal route of administration was as effective as via the intravenous route. On the other hand, oral administration of 30 μg of naloxone resulted in bioavailability equal to only 1.5% that of the same dose given intravenously. Also from TABLE II, it can be seen that the nasal bioavailability of naloxone was nearly 70 times greater than the oral bioavailability.

It also can be seen from TABLE I and the FIGURE of drawing that naloxone was very rapidly absorbed from the nasal mucosa; thus, at the 30 μg dosage level, the peak plasma level was attained in about 5 minutes after instillation of the nose drops. Further, the half-life of elimination of the drug after nasal administration was found to be comparable to its half-life following intravenous nasal administration.

The study described above indicates that naloxone is rapidly absorbed from the nasal mucosa into the systemic circulation without extensive intestinal or first pass metabolism. It is further apparent from this study that the bioavailability of naloxone when administered nasally is equivalent to the bioavailability of the drug when administered intravenously and vastly superior to its bioavailability by the oral route. As the phenolic hydroxyl group in naloxone is believed to be responsible for the extensive metabolism seen when the drug is administered orally and, consequently, for the drug's poor oral bioavailability, it follows that similar improvement in bioavailability for nasal versus oral administration will be observed in the case of the other phenolic drugs intended for use in the method and compositions of the present invention.

Any of the selected drugs intended for use in the present invention, i.e. morphine, THC or one of their pharmacologically active phenolic analogues, can be administered nasally to warm-blooded animals, conveniently by formulation into a nasal dosage form comprising the desired drug, in a therapeutically effective amount (i.e., depending on the selected drug, an analgesically effective amount, an antiemetic effective amount, an amount effective to antagonize the effects of a narcotic agent, etc.), together with a nontoxic pharmaceutically acceptable nasal carrier therefor. This type of composition can be used in the treatment of any of the variety of conditions which are responsive to treatment with the selected drug itself by other routes of administration.

As indicated earlier, in the compositions of the invention, the drug can be employed in the form of the free base or, in the case of morphine and its analogues, in the form of a pharmaceutically acceptable salt thereof. Suitable nontoxic pharmaceutically acceptable nasal carriers will be apparent to those skilled in the art of nasal pharmaceutical formulations. For those not skilled in the art, reference is made to the text entitled "REMINGTON's PHARMACEUTICAL SCIENCES", 14th edition, 1970. Obviously, the choice of suitable carriers will depend on the exact nature of the particular nasal dosage form desired, e.g., whether the drug is to be formulated into a nasal solution (for use as drops or as a spray), a nasal suspension, a nasal ointment or a nasal gel. Preferred nasal dosage forms are solutions, suspensions and gels, which contain a major amount of water (preferably purified water) in addition to the active ingredient. Minor amounts of other ingredients such as pH adjusters (e.g., a base such as NaOH), emulsifiers or dispersing agents, buffering agents, preservatives, wetting agents and jelling agents (e.g., methylcellulose) may also be present. Most preferably, the nasal composition is isotonic, i.e. it has the same osmotic pressure as blood serum. If desired, sustained release nasal compositions, e.g. sustained release gels, can be readily prepared, preferably by employing the desired drug in one of its relatively insoluble forms, such as the free base or an insoluble salt. In the case of morphine and its analogues, when the free base is not sufficiently insoluble for sustained release compositions, or when a more highly insoluble form is desired, a long chain carboxylic acid salt of the desired drug can be conveniently employed. The carboxylic acid portion of the salt preferably contains 10 to 20 carbon atoms. Such salts (e.g. stearates, palmitates etc.) can be readily synthesized, for example, by dissolving the hydrochloride salt of the drug in water, then adding the alkali metal salt of the desired long chain carboxylic acid (e.g. sodium stearate). The corresponding long chain carboxylic acid salt of the drug which precipitates out of the solution is removed by filtration. Alternatively, equimolar amounts of the free base of the drug and the long chain carboxylic acid are combined in methanol. That mixture is then added to a small volume of water, causing the desired salt (e.g. stearate) of the drug to precipitate out.

Examples of the preparation of typical nasal compositions containing selected drugs are set forth below. However, it is to be understood that these examples are given by way of illustration only and are not to be construed as limiting the invention either in spirit or in scope as many modifications both in materials and in methods will be apparent to those skilled in the art.

EXAMPLE 1

1 Gram of naloxone hydrochloride is dissolved in 80 ml of distilled water and the pH of the resultant solution is adjusted to 7.4 with dilute sodium hydroxide solution. A quantity of water sufficient to bring the total volume to 100 ml is then added and sufficient sodium chloride (or other appropriate salt) is added to adjust the solution to isotonicity. The solution is then sterilized by being passed through a 0.2 micron Millipore filter. The final composition contains 1 mg of naloxone hydrochloride per 0.1 ml of solution.

The above procedure is repeated using 1 gram of levallorphan tartrate in place of the naloxone hydrochloride. The resultant composition contains 1 mg of lavallorphan tartrate per 0.1 ml of solution.

Repetition of the procedure of the first paragraph of this example using 5 grams of apomorphine hydrochloride, 3 grams of hydromorphone hydrochloride, 4 grams of metopon hydrochloride, 1.5 grams of oxymorphone hydrochloride, 0.6 grams of buprenorphine hydrochloride, 2 grams of butorphanol tartrate, 3 grams of pentazocine hydrochloride, 3 grams of phenazocine hydrobromide or 5 grams of nalorphine hydrochloride in place of the naloxone hydrochloride affords a nasal composition containing, respectively, 5 mg of apomorphine hydrochloride, 3 mg of hydromorphone hydrochloride, 4 mg of metopon hydrochloride, 1.5 mg of oxymorphone hydrochloride, 0.6 mg of buprenorphine hydrochloride, 2 mg of butorphanol tartrate, 3 mg of pentazocine hydrochloride, 3 mg of phenazocine hydrobromide, or 5 mg of nalorphine hydrochloride, per 0.1 ml of solution.

EXAMPLE 2

15 Grams of nalbuphine hydrochloride are combined with 80 ml of distilled water and the pH is adjusted to 4.5 with dilute sodium hydroxide solution. A quantity of water sufficient to bring the total volume to 100 ml is then added and sufficient sodium chloride is added to adjust the solution to isotonicity. The solution is then sterilized by being passed through a 0.2 micron Millipore filter. The resultant composition contains 15 mg of nalbuphine hydrochloride per 0.1 ml.

The procedure described above is substantially repeated, except that 15 grams of morphine sulfate are used in place of the nalbuphine hydrochloride, affording a nasal composition containing 15 mg of morphine sulfate per 0.1 ml.

Repetition of the procedure of the first paragraph of this example using 20 grams of pentazocine lactate in place of the nalbuphine hydrochloride affords a nasal composition containing 20 mg of pentazocine lactate per 0.1 ml.

EXAMPLE 3

1 Gram of naltrexone is dissolved in 80 ml of isotonic saline solution and the pH of the resultant solution is adjusted to 7.0–7.2 with dilute hydrochloric acid. A quantity of isotonic saline sufficient to bring the total volume to 100 ml is then added, and the solution is sterilized by being passed through a 0.2 micron Millipore filter. The resultant composition contains 1 mg of naltrexone per 0.1 ml.

Repetition of the foregoing procedure utilizing 0.5 gram of levonantradol in place of the naltrexone affords a nasal composition containing 0.5 mg of levonantradol per 0.1 ml.

The procedure of the first paragraph of this example is substantially repeated, save that 4 grams of butorphanol are employed in place of the naltrexone, to afford a nasal composition containing 4 mg of butorphanol per 0.1 ml.

Substitution of 2 grams of cyclazocine for the naltrexone used in the first paragraph of this example and substantial repetition of the procedure there detailed afford a nasal composition containing 2 mg of cyclazocine per 0.1 ml.

EXAMPLE 4

80 Grams of water are heated to 80° C. and 3.0 grams of Methocel are added, with stirring. The resultant mixture is allowed to stand at room temperature for 3 hours. Then, 1.5 grams of naloxone stearate are suspended in 20 grams of water, that suspension is added to the gel and thoroughly mixed, and the resultant viscous solution or gel is adjusted to isotonicity with sodium chloride. The sustained release composition thus obtained contains 1.5 mg of naloxone stearate per 0.1 ml.

The above procedure is substantially repeated, except that 2.0 rather than 3.0 grams of Methocel are employed, and 1.5 grams of naltrexone myristate are substituted for the naloxone stearate. The sustained release composition prepared in this manner contains 1.5 mg of naltrexone myristate per 0.1 ml.

Repetition of the procedure of the first paragraph of this example, but using 20 grams of nalbuphine palmitate in place of the naloxone stearate, affords a sustained release composition containing 20 mg of nalbuphine palmitate per 0.1 ml.

The procedure of the first paragraph of this example is substantially repeated, except that 3 grams of levorphanol stearate are employed in place of the naloxone stearate. The resultant sustained release composition contains 3 mg of levorphanol stearate per 0.1 ml.

Substitution of 4 grams of buprenorphine stearate for the naloxone stearate used in the first paragraph of this example and substantial repetition of the procedure there detailed afford a sustained release composition containing 4 mg of buprenorphine stearate per 0.1 ml.

In a similar manner, repetition of the procedure of the first paragraph of this example, but using 2.5 grams of butorphanol palmitate, 3.5 grams of pentazocine myristate, 10 grams of THC, 20 grams of CBD or 1 gram of levonantradol in place of the naloxone stearate affords a sustained release composition containing, respectively, 2.5 mg of butorphanol palmitate, 3.5 mg of pentazocine myristate, 10 mg of THC, 20 mg of CBD or 1 mg of levonantradol, per 0.1 ml.

EXAMPLE 5

The following are illustrative aqueous solutions of selected drugs suitable for use as nasal drops or nasal spray. In each case, the pH of the final composition is adjusted to 7.4. If desired, the solutions are adjusted to isotonicity.

| COMPOSITION A | |
|---|---|
| Ingredient | Amount |
| nalbuphine hydrochloride | 1000 mg |
| Tween 80 | 4 mg |
| methylcellulose | 40 mg |
| water, purified | 10 ml |

| COMPOSITION B | |
|---|---|
| Ingredient | Amount |
| nalorphine hydrobromide | 500 mg |
| Tween 80 | 3 mg |
| methylcellulose | 30 mg |
| water, purified | 10 ml |

| COMPOSITION C | |
|---|---|
| Ingredient | Amount |
| buprenorphine hydrochloride | 100 mg |
| Tween 80 | 2 mg |
| methylcellulose | 20 mg |
| water, purified | 10 ml |

Naturally, the therapeutic dosage range for nasal administration of the drugs according to the present invention will vary with the size of the patient, the condition for which the drug is administered and the particular drug employed. Generally, the daily dosage will approximate the amounts previously employed for IV, IM or SC administration of the particular drug involved. Thus, a typical dose of buprenorphine would be 4–8 mg per day as a maintenance dose in the treatment of narcotic addicts. The quantity of nasal dosage form needed to deliver the desired dose will of course depend on the concentration of drug in the composition. The volume of solution or gel which would be needed to deliver the daily dose of buprenorphine specified above would be 0.1 to 0.2 ml of 4% solution or gel.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method for eliciting an analgesic or narcotic antagonist response in a warm-blooded animal, which comprises nasally administering to said animal:
  (a) to elicit an analgesic response, an analgesically effective amount of morphine, hydromorphone, metopon, oxymorphone, desomorphine, dihydromorphine, levorphanol, cyclazocine, phenazocine, levallorphan, 3-hydroxy-N-methylmorphinan, levophenacylmorphan, metazocine, norlevorphanol, phenomorphan, nalorphine, nalbuphine, buprenorphine, butorphanol or pentazocine, or a nontoxic pharmaceutically acceptable acid addition salt thereof; or
  (b) to elicit a narcotic antagonist response, a narcotic antagonist effective amount of naloxone, naltrexone, diprenorphine, nalmexone, cyprenorphine, levallorphan, alazocine, oxilorphan, cyclorphan, nalorphine, nalbuphine, buprenorphine, butorphanol, cyclazocine or pentazocine, or a nontoxic pharmaceutically acceptable acid addition salt thereof.

2. A method according to claim 1 for eliciting a narcotic antagonist response in a warm-blooded animal, which comprises nasally administering to said animal a narcotic antagonist effective amount of naxolone, naltrexone, diprenorphine, nalmexone, cyprenorphine, levallorphan, alazocine, oxilorphan, cyclorphan, nalorphine, nalbuphine, buprenorphine, butorphanol, cyclazocine or pentazocine, or a nontoxic pharmaceutically acceptable acid addition salt thereof.

3. The method according to claim 2 wherein the compound administered is naloxone, naltrexone, nalorphine, nalbuphine, buprenorphine, diprenorphine, nalmexone or cyprenorphine, or a nontoxic pharmaceutically acceptable acid addition salt thereof.

4. The method according to claim 2 wherein the compound administered is in the form of a long-chain carboxylic acid salt, the carboxylic acid portion of the salt containing from 10 to 20 carbon atoms.

5. The method according to claim 4 wherein the long chain carboxylic acid salt is a stearate, palmitate or myristate.

6. The method according to claim 3 wherein the compound administered is naloxone or a nontoxic pharmaceutically acceptable acid addition salt thereof.

7. The method according to claim 3 wherein the compound administered is naltrexone or a nontoxic pharmaceutically acceptable acid addition salt thereof.

8. The method according to claim 3 wherein the compound administered is nalorphine or a nontoxic pharmaceutically acceptable acid addition salt thereof.

9. The method according to claim 3 wherein the compound administered is nalbuphine or a nontoxic pharmaceutically acceptable acid addition salt thereof.

10. The method according to claim 3 wherein the compound administered is buprenorphine or a nontoxic pharmaceutically acceptable acid addition salt thereof.

11. A method according to claim 1 for eliciting an analgesic response in a warm-blooded animal which comprises nasally administering to said animal an analgesically effective amount of nalorphine, nalbuphine, buprenorphine, butorphanol, cyclazocine, levallorphan or pentazocine, or a nontoxic pharmaceutically acceptable acid addition salt thereof.

12. The method according to claim 11 wherein the compound administered is in the form of a long chain carboxylic acid salt, the carboxylic acid portion of the salt containing from 10 to 20 carbon atoms.

13. The method according to claim 12 wherein the long chain carboxylic acid salt is a stearate, palmitate or myristate.

14. The method according to claim 11 wherein the compound administered is buprenorphine or a nontoxic pharmaceutically acceptable acid addition salt thereof.

15. A method according to claim 1 for eliciting an analgesic response in a warm-blooded animal, which comprises nasally administering to said animal an analgesically effective amount of morphine, hydromorphone, metopon, oxymorphone, desomorphine, dihydromorphine, levorphanol, phenazocine, 3-hydroxy-N-methylmorphinan, levophenacylmorphan, metazocine, norlevorphanol or phenormorphan, or a nontoxic pharmaceutically acceptable acid addition salt thereof.

16. The method according to claim 15 wherein morphine is administered, in the form of the free base or a nontoxic pharmaceutically acceptable acid addition salt thereof.

17. The method according to claim 15 wherein hydromorphone, metopon, oxymorphone, desomorphine, dihydromorphine, levorphanol, phenazocine, 3-hydroxy-N-methylmorphinan, levophenacylmorphan, metazocine, norlevorphanol or phenomorphan is administered, in the form of the free base or a nontoxic pharmaceutically acceptable acid addition salt thereof.

18. The method according to claim 17 wherein the compound administered is hydromorphone, metopon or oxymorphone, or a nontoxic pharmaceutically acceptable acid addition salt thereof.

19. The method according to claim 15 wherein the compound administered is in the form of a long chain carboxylic acid salt, the carboxylic acid portion of the salt containing from 10 to 20 carbon atoms.

20. A method according to claim 2 wherein the compound administered is butorphanol, pentazocine, cyclazocine or oxilorphan, or a nontoxic pharmaceutically acceptable acid addition salt thereof.

21. The method according to claim 20 wherein the compound administered is butorphanol or a nontoxic pharmaceutically acceptable acid addition salt thereof.

22. A method according to claim 11 wherein the compound administered is butorphanol, cyclazocine or pentazocine, or a nontoxic pharmaceutically acceptable acid addition salt thereof.

23. The method according to claim 17 wherein the compound administered is levorphanol or a nontoxic pharmaceutically acceptable acid addition salt thereof.

24. The method according to claim 1 wherein the compound administered is morphine, oxymorphone, buprenorphine, naloxone, nalorphine, nalbuphine, naltrexone, hydromorphone, metopon, nalmexone, cyprenorphine or diprenorphine, or a nontoxic pharmaceutically acceptable acid addition salt thereof.

25. The method according to claim 24 wherein the compound is in the form of a long-chain carboxylic acid salt, the carboxylic acid portion of the salt containing from 10 to 20 carbon atoms.

26. The method according to claim 25 wherein the long-chain carboxylic acid salt is a stearate, palmitate or myristate.

27. The method according to claim 1 wherein the compound administered is levorphanol, cyclazocine, phenazocine, butorphanol, pentazocine or oxilorphan, or a nontoxic pharmaceutically acceptable acid addition salt thereof.

28. The method according to claim 27 wherein the compound is in the form of a long-chain carboxylic acid salt, the carboxylic acid portion of the salt containing from 10 to 20 carbon atoms.

29. The method according to claim 28 wherein the long-chain carboxylic acid salt is a stearate, palmitate or myristate.

30. A pharmaceutically acceptable nasal dosage form for eliciting an analgesic response in a warm-blooded animal, which comprises (i) an analgesically effective amount of morphine, hydromorphone, metopon, oxymorphone, desomorphine, dihydromorphine, levorphanol, cyclazocine, phenazocine, 3-hydroxy-N-methylmorphinan, levophenacylmorphan, metazocine, norlevorphanol, phenomorphan, nalorphine, nalbuphine, buprenorphine, butorphanol, levallorphan or pentazocine, or a nontoxic pharmaceutically acceptable acid addition salt thereof, and (ii) a nontoxic pharmaceutically acceptable nasal carrier therefor, said nasal dosage form comprising a nasal ointment or a nasal gel.

31. A dosage form according to claim 30, said dosage form comprising a nasal ointment.

32. A dosage form according to claim 30, said dosage form comprising a nasal gel.

33. A dosage form according to claim 32, said dosage form comprising a sustained release nasal gel.

34. A dosage form according to claim 30, wherein (i) comprises an analgesically effective amount of morphine or buprenorphine, or of a nontoxic pharmaceutically acceptable acid addition salt of morphine or buprenorphine.

35. A dosage form according to claim 30, wherein the compound administered is in the form of a long chain carboxylic acid salt, the carboxylic acid portion of the salt containing from 10 to 20 carbon atoms.

36. A pharmaceutically acceptable nasal dosage form for eliciting a narcotic antagonist response in a warm-blooded animal, which comprises (i) a narcotic antagonist effective amount of naloxone, naltrexone, diprenorphine, nalmexone, cyprenorphine, levallorphan, alazocine, oxilorphan, cyclorphan, nalorphine, nalbuphine, buprenorphine, butorphanol, cyclazocine or pentazocine, or a nontoxic pharmaceutically acceptable acid addition salt thereof, and (ii) a nontoxic pharmaceutically acceptable nasal carrier therefor, said nasal dosage form comprising a nasal ointment or a nasal gel.

37. A dosage form according to claim 36, said dosage form comprising a nasal ointment.

38. A dosage form according to claim 36, said dosage form comprising a nasal gel.

39. A dosage form according to claim 38, said dosage form comprising a sustained release nasal gel.

40. A dosage form according to claim 36, wherein (i) comprises a narcotic antagonist effective amount of naloxone, naltrexone, nalorphine, nalbuphine or buprenorphine, or of a nontoxic pharmaceutically acceptable acid addition salt of naloxone, naltrexone, nalorphine, nalbuphine or buprenorphine.

41. A dosage form according to claim 36, wherein the compound administered is in the form of a long chain carboxylic acid salt, the carboxylic acid portion of the salt containing from 10 to 20 carbon atoms.

42. A pharmaceutically acceptable sustained release nasal dosage form for nasally delivering systemic therapeutic levels of drug to a warm-blooded animal which comprises (i) a systemically therapeutically effective amount of a long chain carboxylic acid salt of morphine, hydromorphone, metopon, oxymorphone, desomorphine, dihydromorphine, levorphanol, cyclazocine, phenazocine, 3-hydroxy-N-methylmorphinan, levophenacylmorphan, metazocine, norlevorphanol, phenomorphan, nalorphine, nalbuphine, buprenorphine, butorphanol, pentazocine, naloxone, naltrexone, diprenorphine, nalmexone, cyprenorphine, levallorphan, alazocine, oxilorphan or cyclorphan, and (ii) a nontoxic pharmaceutically acceptable nasal carrier therefor.

43. A dosage form according to claim 42, wherein (i) comprises a systemically therapeutically effective amount of a long chain carboxylic acid salt of naloxone, naltrexone, nalorphine, nalbuphine or buprenorphine.

44. A dosage form according to claim 42, wherein the carboxylic acid portion of said salt contains 10 to 20 carbon atoms.

45. A dosage form according to claim 44, wherein said salt is a stearate, palmitate or myristate.

46. A dosage form according to claim 42, said dosage form comprising a nasal solution, nasal suspension, nasal ointment or nasal gel.

47. A dosage form according to claim 42, wherein (i) comprises a systemically therapeutically effective amount of a long chain carboxylic acid salt of levorphanol, cyclazocine, phenazocine, butorphanol, pentazocine or oxilorphan.

48. A method for eliciting an analgesic response in a warm-blooded animal, which comprises nasally administering to said animal an analgesically effective amount of a pharmaceutically acceptable nasal dosage form as claimed in claim 30.

49. A method for eliciting a narcotic antagonist response in a warm-blooded animal, which comprises nasally administering to said animal a narcotic antagonist effective amount of a pharmaceutically acceptable nasal dosage form as claimed in claim 36.

50. A dosage form according to claim 36, wherein (i) comprises a narcotic antagonist effective amount of butorphanol, pentazocine, cyclazocine or oxilorphan, or of a nontoxic pharmaceutically acceptable acid addition salt of butorphanol, pentazocine, cyclazocine or oxilorphan.

51. A dosage form according to claim 30, wherein (i) comprises an analgesically effective amount of levorphanol, cyclazocine, phenazocine, butorphanol or pentazocine, or of a nontoxic pharmaceutically acceptable acid addition salt of levorphanol, cyclazocine, phenazocine, butorphanol or pentazocine.

* * * * *